United States Patent [19]

Moore

[11] Patent Number: 5,645,851
[45] Date of Patent: Jul. 8, 1997

[54] PRODUCT FOR ALLEVIATING THE SYMPTONS OF ARTHRITIS IN MAMMALS

[76] Inventor: Eugene R. Moore, 5600 Woodview Pass, Midland, Mich. 48642

[21] Appl. No.: 629,744

[22] Filed: Apr. 9, 1996

Related U.S. Application Data

[63] Continuation-in-part of Ser. No. 202,723, Feb. 28, 1994, Pat. No. 5,529,786.
[51] Int. Cl.⁶ .............................. A61K 9/10; A61K 9/20; A61K 35/32; A61K 35/44
[52] U.S. Cl. ................. 424/439; 424/441; 424/464; 424/548; 424/571; 514/801; 514/825
[58] Field of Search ........................ 424/439, 441, 424/464, 548, 571; 514/801, 825

[56] References Cited

U.S. PATENT DOCUMENTS 3,632,350   1/1972   Battista ................................. 99/1

*Primary Examiner*—Thurman K. Page
*Assistant Examiner*—James M. Spear
*Attorney, Agent, or Firm*—Merlin B. Davey

[57] ABSTRACT

This invention provides a composition useful as an edible supplement for alleviating the symptoms of arthritis for oral consumption by mammals, said composition comprising animal tissue containing water-insoluble Type II collagen, which has been separated from non-Type II collagen containing tissue and has been sterilized in subdivided form without changing the original structure of the Type II collagen.

13 Claims, No Drawings

PRODUCT FOR ALLEVIATING THE SYMPTOMS OF ARTHRITIS IN MAMMALS

CROSS REFERENCE TO RELATED APPLICATIONS

This application is a continuation in-part of application Ser. No. 202,723 filed 28 Feb. 1994, U.S. Pat. No. 5,529,786.

FIELD OF THE INVENTION

The present invention pertains to means for treating the symptoms of autoimmune arthritis in mammals and, more particularly, relates to means for preparing animal tissue for oral administration to mammals, compositions comprising said animal tissue and methods for alleviating the symptoms of autoimmune arthritis, particularly rheumatoid arthritis, in humans.

BACKGROUND OF THE INVENTION

Autoimmune arthritis, and particularly rheumatoid arthritis, is a painful and often crippling disease that initially results in swollen and inflammed joints, but often progresses to deformed or completely destroyed joints. This is a result of the body mistakenly attacking collagen, which is the major portion of cartilage tissue. Cartilage tissue serves the function of a lubricant in the joints, keeping bone from rubbing on bone. As the disease progresses and more of the cartilage is destroyed, bone does begin to wear on bone. This results in even more severe pain and ultimately destruction of the joint itself. As the disease progresses, the body sometimes attacks other collagen in the soft tissues of the body which can cause a variety of arthritis-related diseases.

In order to initiate the disease, it is apparent that an individual must have an inherent (perhaps genetic) susceptibility. Given this susceptibility, there is now strong evidence that the disease is initiated by exposure to the Epstein-Bart virus. The ability of the Epstein-Bart virus to initiate Rheumatoid Arthritis has been linked to a key amino acid sequence which is identical to a sequence found in human collagen. Thus, in generating antibodies to destroy the Epstein-Bart virus, the body generates antibodies that are also capable of attacking its own collagen. In a similar manner, arthritis has been initiated in rats by the intradermal injection of water-soluble highly purified Type II procollagen extracted from chicken cartilage or by the well known complete Freund Adjuvant.

It was also shown that rats could be prevented from getting arthritis or the effects greatly reduced from this injection of water-soluble highly purified procollagen. This was accomplished by feeding the same water-soluble highly purified procollagen to the rats for several days prior to the injection. It was also shown with rats that, once arthritis had been induced, the effects of the disease could be reduced by the oral administration of the same water-soluble highly purified procollagen. In a later study with humans having severe arthritis it has been shown as disclosed in U.S. Pat. No. 5,399,347 that the oral administration of the water-soluble highly purified procollagen is similarly beneficial to humans in reducing the effects of the disease.

While this oral treatment with water-soluble highly purified procollagen represents a long sought and highly desired treatment for Rheumatoid Arthritis, the required water-soluble highly purified Type II procollagen is very difficult to prepare. Typically, it is extracted from the tiny xiphoid cartilages of 2.5 week old chicks. In a preparation of the past art, eighty animals are required to produce 19 g of cleaned xiphoid cartilage dissected free of surrounding tissue. It is typical of the past art to perform up to seven extractions on each batch of tissue to obtain water-soluble procollagen of the required purity.

The procedure of the past art is thus seen to have several serious deficiencies. An extremely large number of animals are required to obtain a small amount of the desired product. The purification procedure is very time consuming and complicated, requiring breakdown by depolymerization of the molecular structure of the Type II collagen in the cartilage. This is followed by multiple extractions and precipitations. These multiple operations, in addition to being time consuming, difficult, and changing the molecular structure, offer many opportunities for microbiological contamination which would render the water-soluble highly purified procollagen unusable or even dangerous. Often an ultra filtration operation is required to remove contamination from the solubilized product prior to the final precipitation. These complications make the water-soluble highly purified procollagen unavailable to many sufferers of arthritis.

SUMMARY OF THE INVENTION

I have found that animal tissue containing water-insoluble undenatured Type II collagen, that is, collagen that has been sterilized without substantially altering its chemical or molecular structure or nature, can be successfully utilized in directly treating arthritis, and particularly autoimmune and more particularly rheumatoid arthritis in mammals. In contrast to the use of water-soluble, highly purified Type II procollagen of the prior art, the use of undenatured insoluble Type II collagen avoids the need of complex purification.

I have further found that said animal tissue containing water-insoluble undenatured Type II collagen can be incorporated in suitable means, such as digestible food, for mammalian ingestion.

The use of undenatured Type II collagen in combination with other substances, such as, for example, antigens, contained in the animal tissue, furthermore, is believed to enhance the activity and effectiveness of the Type II collagen contained in the animal tissue.

DETAILED DESCRIPTION

The animal tissue advantageously employed in the practice of this invention is poultry cartilage, preferably chicken cartilage as obtained from chicken less than about one year of age, although other warm-blooded animal tissue containing Type II collagen, such as turkey cartilage, bovine cartilage and the vitreous humor of eyes, may be employed if desired. In preparing the poultry or warm-blooded animal tissue for oral administration the Type II collagen containing tissue is first dissected free of surrounding tissues and diced or otherwise comminuted by means known in the art desirably into particles no larger than a dose. The particulated cartilage is sterilized by means which do not affect or denature the structure of a major portion of the Type II collagen in the tissue and formed into doses containing therapeutically effective levels of undenatured Type II collagen, said levels being generally in the amount of at least about 0.01 gram and preferably from about 0.1 to about 0.5 grams of animal tissue in a dose. Being a natural product some variation from sample to sample is to be expected. These variations can be minimized by blending after comminution. The blending can be aided by analytical techniques that are known in the art which allow the measurement of the amount of undenatured Type II collagen and other antigens. These measurements will allow blending of batches to obtain uniformity and in some cases to modify potency by increasing certain antigen levels by mixing cartilage from different sources. The optimum dosage may vary and is readily determined by means known in the art. The effective use of a broader range of undenatured Type II collagen containing animal tissue is surprising in view of the prior art which has utilized principally only chicks of less than three weeks of age to depolymerize, extract the water-soluble portion and then highly purify the Type II procollagen. The usefulness of the more mature chickens allows an almost 100 fold increase in the amount of harvestable undenatured Type II collagen from a single animal. This, of course, makes the desired product more readily available in therapeutic quantities, and also greatly decreases the possibility of microcontamination due to the reduced handling during separation from relatively few animals.

A critical step in the utilization of animal tissue to alleviate symptoms of arthritis is the sterilization of the animal tissue either before or after comminution, thus it is essential that a sterilization procedure is employed which maintains the water insoluble structure of the Type II collagen in the animal tissue and also does not involve the denaturization of the Type II collagen in the animal tissue. Treating the animal tissue at elevated temperatures with water, such as exposing the tissue to boiling water substantially decreases the effectiveness of the animal tissue by causing the Type II collagen to become denatured. The treatment with acid causes the Type II collagen to become depolymerized into the less desirable water-soluble Type II procollagen. Preferred methods of sterilizing the comminuted tissue includes washing the comminuted Type II collagen with an oxidizing agent such as hydrogen peroxide or sodium hypochlorite. Exposure to radiation is also a desirable means of sterilizing the Type II collagen.

The utilization of the animal tissue of the present invention involves the oral administration of the comminuted undenatured Type II collagen in the form of animal tissue containing such. By oral administration is meant any form of administration which does not bypass the stomach. Although the invention is not to be construed as being limited to such, the animal tissue of the present invention is principally utilized in the treatment of autoimmune athritis and particularly rheumatoid arthritis as well as in the alleviation of the symptoms of arthritis in all mammals. It is to be understood that the present invention is not to be construed as being limited to the attenuation of all such symptoms in a patient but includes the attenuation or alleviation of even a single symptom. Symptoms alleviated by the treatment in accordance with the present invention include joint tenderness, joint swelling, morning stiffness, grip strength reduction, and in general painful moving of limbs.

The amount of animal tissue involved in a dose consumed at any given time will vary with the purpose of the consumption, the severity of the autoimmune arthritis or its symptoms, as well as the condition, age, weight, medical history and general physical characteristics of the patient to be treated. Consequently the doses, the frequency and time period over which the doses are administered will vary widely. It is not necessary for a single dose to contain an effective dose, although that is of course preferred, if multiple doses can be administered. The animal tissue dose of the present invention may be extended by combination with other digestible ingredients such as in the form of aqueous dispersions, such as milk, or in combination with other proteinaceous substances, sugars, and starches. It may advantageously be administered directly as a comminuted solid as in an encapsulated comminuted solid, as a compression formed pill, as well as a slurry with or without other digestible compositions such as, for example, foodstuffs. It may be packaged in a sterile manner or sterilized after packaging and may be stored at room temperature or reduced temperature. Alternately it may be stored at subfreezing temperature to prevent spoilage and may be frozen with other food substances in concentrated form.

The following examples further illustrate the present invention:

EXAMPLE 1.

A chicken purchased from the grocery store is assumed to have been raised under the strict governmental regulations which prevent sick or diseased chickens from entering the food supply. A never frozen chicken is purchased and washed well with a dilute detergent solution, then soaked for 20 minutes in a 400 ppm chlorine equivalent solution provided by addition of 8.01 g of a 5.15% solution of sodium hypochlorite solution of 1000 gm of water. Surface contamination is mostly removed or destroyed by this treatment. The knife to be used to remove the cartilage is sterilized by washing well, then exposing the blade briefly to a flame. Clean rubber gloves are used as the cartilage is carefully cut away from the chicken flesh, then clean paper towel is used to dry and wipe the cartilage clean of loosely adhering material. Soaking in 3% hydrogen peroxide solution for over 20 minutes further sterilizes the cartilage without denaturing the collagen. The cartilage can then be stored at home freezer temperatures in double Zip-Loc (Reg. TM) brand polyethylene bags. The cleanliness of the procedure is verified by placing some of the cartilage into sterility bottles (Fisher Scientific, Code #99100) at 35° C. for 24 hours. The lack of turbidity 5 indicates a lack of microorganisms. Prior to ingestion, the cartilage tissue is removed from low temperature storage, carefully diced with a cleaned razor blade and separated into 0.1 g or 0.5 g portions.

EXAMPLE 2

Safety is tested by ingestion of 0.5 g of the diced cartilage daily by a healthy male for one week during which time no gastrointestinal abnormalities are noted.

EXAMPLE 3

Effectiveness is judged from the effect of oral ingestion of the diced cartilage in breakfast juice by a mature, 135-pound female suffering from severe rheumatoid polyarthritis. Ingestion is continued for a period of four months. The dose is 0.1 g/day for the first month and 0.5 g/day for the remaining three months. The dose is initially given each morning at least 20 minutes before breakfast, on an empty stomach. After a few days the dose time is varied randomly and the type of juice is varied, usually orange or cranberry. It is noted toward the end of the study that the patient is gradually able to reduce the intake of her normal arthritis medicine (Lodine) without ill effect. During this treatment time a general decrease in pain in all joints is noted. Particularly, the ankle and knee joints are noted to be less swollen and painful. Black and blue marks in the ankle areas are seen to be significantly diminished. Higher energy levels are noted.

EXAMPLE 4

In a manner similar to Example 3, bovine cartilage is employed with similar desirable results.

EXAMPLE 5

Bovine vitreous humor (eye) tissue is used after being prepared by careful dissection, blending, and centrifuging to obtain a solid pellet which is employed with similar desired results.

EXAMPLE 6

Cartilage is prepared as in Example 1, except after being diced it is sterilized by two techniques to enable its shelf life to be extended without low temperature storage:

a. The diced cartilage is soaked in a 3% solution of hydrogen peroxide for about 20 hours, then surface moisture removed and dose size quantities stored in polyethylene bags an extended period of time at room temperature.

b. The diced cartilage is placed in polyethylene bags for sterilization by electron beam radiation. A wide variety of electron doses is used. The exact electron dose is not known but by variation of time under the electron beam of constant intensity, it is possible to understand relative doses of electrons. Samples with the basic dose are increased in increments of 1×, 2×, 3× to 10× and 100×. These samples are stored for an extended period of time at room temperature.

Samples from both a and b are judged for both sterility and effectiveness. Sterility is judged by obvious discoloration of the samples (unsterile if discolored) or by the use of sterility bottles as described in Example 1 for samples that were not discolored. Samples are judged for effectiveness using the same procedure as in Example 3. The results are summarized in Table I.

TABLE I

| Type of Sterilization | Dose | Sterility | Effectiveness |
| --- | --- | --- | --- |
| electron beam | 1× | no | not tested |
| electron beam | 2× | no | not tested |
| electron beam | 3× | ? | not tested |
| electron beam | 4× | ? | not tested |
| electron beam | 5× | yes | yes |
| electron beam | 6× | yes | yes |
| electron beam | 7× | yes | yes |
| electron beam | 8× | yes | yes |
| electron beam | 9× | yes | yes |
| electron beam | 10× | yes | yes |
| electron beam | 100× | yes | no |
| peroxide | 20 hrs. | yes | yes |

The results of Example 6 demonstrate that shelf life can be extended by two of the common techniques used for sterilization which do not denature the structure of the Type II collagen in the tissue. It is anticipated that other techniques that will be apparent to those familiar with the sterilization art may also be used to extend shelf life if utilized within the proper range as shown by the example above. Too strong a treatment can denature the cartilage and render it ineffective, while too little will not completely enough sterilize. In each case, the best level of the sterilization treatment can be determined by the simple experimentation as determined above or by use of laboratory animals as described in the art. In many cases, it will be desirable to package or encapsulate the cartilage before or after the sterilization treatment. While the above sterilization techniques will serve to extend the cartilage shelf life, refrigerated storage may be used to extend it even further. The packaging or encapsulation will serve to make the precise dose easier to distribute and administer to patients. This is a very important aspect of making the treatment available to the large number of people who suffer from arthritis.

EXAMPLE 7

Cartilage is prepared as in Example 1, except after being diced it is encapsulated and then sterilized using the 7× electron beam treatment of Example 6.

a. The first technique for encapsulating involves use of preformed gelatin capsules that were previously prepared in such a way that they come apart to allow insertion of a dose or fraction of a dose into them. They have the shape of two cylinders, each with one rounded closed end and one rounded open end. The diameter of each cylinder is such that the outside diameter of one is the same or slightly smaller than the inside diameter of the other. When they are apart, the desired dose of cartilage is placed within the smaller diameter end and the other end slid over top to completely close the capsule with the cartilage inside. This is repeated until a number of capsules have been filled. The filled capsules are subjected to a 7× treatment of electron beam radiation as in Example 6, then tested for effectiveness in treatment of Rheumatoid Arthritis.

b. The second technique for encapsulation utilizes a gelatin solution to coat the diced particles of cartilage. The solution is prepared by dissolving 10 parts of a household gelatin (sold under the trade name of JELL-O by the General Foods Corporation of New York) into 8.7 parts of pure water. Dissolution takes place when heated to boiling in a microwave oven with periodical stirring. After dissolution is complete the solution is cooled slightly, then poured over single doses of diced cartilage on waxed paper. After thoroughly mixing (during cooling) until all the cartilage is coated, the material is formed into as small an area as possible and allowed to cool, which sets the shape. After sterilization as in 7(a), these capsules containing sterilized cartilage are found to be effective in treatment of Rheumatoid Arthritis. They are seen to have both the advantage of increased shelf life and that of convenience of use.

EXAMPLE 8

Samples are prepared in accordance with sample a and b of Example 7 except instead of electron beam sterilization after being encapsulated, they are sterilized chemically prior to being encapsulated. Cartilage is sterilized by placement in a 3% solution of hydrogen peroxide for 10 hours, then surface moisture removed before encapsulation. Both samples are found to have the triple benefits of an increased shelf life, convenience of dosing and consuming and effectiveness in treatment of Rheumatoid Arthritis.

EXAMPLE 9

Samples are prepared and tested as in Example 8 except the 5.25% sodium hypochlorite diluted solution of Example 1 is used for sterilization. Beneficial results similar to Example 8 are obtained.

EXAMPLE 10

Samples are prepared and tested as in Example 8 except gaseous ethylene oxide is used for sterilization. Beneficial results similar to Example 9 are also obtained.

EXAMPLE 11

Cartilage is prepared as in Example 1, except instead of being diced by hand, the cartilage is ground in the presence of liquid nitrogen. The resulting fine ground cartilage is then sterilized with hydrogen peroxide as in Example 1 and then made into a tablet shape by:

a. adding 15% of cornstarch paste as a binder and 15% calcium silicate as a disintegrator, to a dough mixer (AMF powder and dough mixer) and mixing until homogeneous;

b. the material is granulated while still wet;

c. the prepared wet granules are dried in a electric granule dryer at 60 degrees C., particles larger than 16 mesh were removed and ground to pass a 16 mesh screen;

d. the granules are mixed with 0.5% magnesium stearate as a lubricant and tablets are compressed on a tablet press machine using concave punches. Samples are found to have the same advantages as found in Example 10.

EXAMPLE 12

In a manner similar to Example 7(a), the cartilage is prepared then, prior to encapsulation, dryed in an air oven at an average temperature of 110° F. until more than half its weight in water is lost. The samples are found to have the same advantages as Example 7(a) with the added advantages of improved shelf life, reduced volume, and better solids handling characteristics (which allows automatic capsule or container filling).

EXAMPLE 13

Cartilage is prepared as in Example 1. Effectiveness is judged from the effect of oral ingestion by a mature dog that is suffering from severe rheumatoid arthritis with several inflamed joints that cause difficulty walking. The weight of the dog is 53 pounds and an effective amount of cartilage is orally ingested daily by the dog for a period of three months. This amount is 0.03 gram/day for the first 30 days and it is then increased to 0.15 gram/day for the remainder of the study. This effective amount is administered as a food supplement. After a period of 40 days it is noted that the dog is walking with significantly less difficulty and that the inflamed joints are significantly improved.

In some cases the cartilage is mixed with hamburger and fed as a semi-solid mixture. In other cases it is mixed with liquid supplements which contain other nutrients such as milk products as well as attractive tasting material such as beef or chicken extracts, aseptically packaged and stored at room temperature prior to use.

EXAMPLE 14

Cartilage is prepared as in Example 1. Effectiveness is judged from the effect of oral injection, over a period of three months, by six laboratory rats that have been induced with severe arthritis using the well known complete Freund Adjuvant. Cartilage amounts are reduced from that of example 5A. to maintain about the same amount per body weight. The cartilage is introduced directly into the mammals stomach (using a tube and syringe) as a liquid suspension containing other desired supplements. At the end of the three month period a measurable reduction in the effects of arthritis is found on all the animals except one.

The advantages of packaging or encapsulating are well known in the art surrounding pharmaceutical technology, flavor and odor technology, and the art of insecticides and herbicides. Techniques for forming tablets using a variety of binders, disintegrating agents and lubricants and other additives are described in detail by M. H. Rubinstein in his book "Pharmaceutical Technology, Tabulating Technology", Volume 1, John Wiley and Sons, N.Y., 1987). Many of the well known techniques for encapsulating are explained in detail by Risch and Reineccius in the book, "Flavor Encapsulation", ACS Symposium Series 370, Am. Chem. Soc., Washington, D.C., 1988 and by M. H. Gutcho in the book "Microcapsules and Microencapsulation Techniques", Noyes Data Corp., New Jersey, 1976. As pointed out in these references, a wide variety of water soluble, food grade, polymeric materials may be used for encapsulating coatings. These may include carbohydrate and protein natural materials as well as synthetics such as polyvinyl alcohol, methylcellulose, and base soluble copolymers of maleic anhydride or acrylic acid. Protein based materials would include gelatin and gelatin derivatives, polypeptone, soy protein, and milk derived protein. Carbohydrate based agents would include hydrolized starches, lipophilic starches, and plant exudates. The teachings of these references are included herein by reference.

Both batch drying and fluid bed drying may be used to combine the cartilage with the polymeric agents. While tray drying is slower, it offers the opportunity for agglomeration followed by grinding to preferred sizes. Fluid bed drying while coating with a spray allows nearly the originally particle sizes to be maintained.

The performance of the cartilage may be enhanced by the use of controlled release coatings. Typically, particles of cartilage would be coated with varying thicknesses of a slow dissolving coating. The thinner coatings would be dissolved instantly, while the thicker layers would require up to 12 hours to dissolve.

While the preferred minimal dose is from 0.1 to 0.5 g of cartilage per day, for average weight adults, the adminstered dosage can vary widely without side effects as long as a minimal therapeutic dose is maintained. There are no adverse effects observed with doses ten fold or more higher than stated above. It is usuallly desirable ultimately to discontinue conventional medication such as immune system depression medication for arthritis in order to eliminate the undesired side effects associated with those immune system depression drugs. Other than side effects, however, there is no apparent need to discontinue the old medication before starting the cartilage treatment. The ability to continue the old medication while starting the new cartilage treatment provides the benefit of avoiding the frequent "arthritis shock" produced while switching medication.

As illustrated by Example 3 of the present specification, the undenatured Type II collagen may be ingested along with various liquid or solid foods or included in foods sold in containerized form.

Various modifications may be made in the present invention without departing from the spirit or scope thereof as will be readily apparent to those skilled in the art.

I claim:

1. A composition useful as an edible supplement for alleviating the symptoms of arthritis for oral consumption by mammals, said composition comprising at least on one member of the group consisting of cartilage add vitreous humor derived from warm blooded animals and containing water-insoluble Type II collagen, which has been separated from non-Type II collagen containing tissue and has been sterilized without changing the original structure of the Type II collagen.

2. Composition of claim 1 containing at least 0.01 gram of animal tissue.

3. Composition of claim 2 containing at least 0.1 g of animal tissue.

4. Composition of claim 2 in the form of a suspension in a liquid medium.

5. Composition of claim 2 in the form of a supplement to solid food.

6. Composition of claim 1 wherein the animal tissue is poultry tissue.

7. Composition of claim 5 wherein the poultry tissue is chicken tissue.

8. Composition of claim 1 wherein the animal tissue is bovine cartilage.

9. Composition of claim 1 wherein the animal tissue is bovine vitreous humor.

10. Composition of claim 4 wherein the liquid medium is a fruit juice.

11. Composition of claim 4 wherein the liquid medium is milk.

12. Composition of claim 5 wherein the solid food is a dairy product.

13. Composition of claim 5 wherein the solid food is a meat product.

* * * * *

UNITED STATES PATENT AND TRADEMARK OFFICE
CERTIFICATE OF CORRECTION

PATENT NO. : 5,645,851
DATED : July 8, 1997
INVENTOR(S) : Moore

It is certified that error appears in the above-indentified patent and that said Letters Patent is hereby corrected as shown below:

Title page item [54] and col. 1, line 2,

In the title the word symptoms was misspelled (two places).

In Claim 1, line 3, delete "on".

In Claim 1, line 4, delete "add" and insert --and--

In Column 4, line 35, delete "5".

Signed and Sealed this

Eighteenth Day of November 1997

Attest:

BRUCE LEHMAN

Attesting Officer

Commissioner of Patents and Trademarks